United States Patent [19]

Sih et al.

[11] Patent Number: 4,873,337
[45] Date of Patent: Oct. 10, 1989

[54] N-SUBSTITUTED DERIVATIVES OF 2-(PYRIDYLALKENESULFINYL) BENZIMIDAZOLES AS GASTRIC ANTISECRETORY AGENTS

[75] Inventors: John C. Sih; Moo J. Cho, both of Kalamazoo, Mich.

[73] Assignee: The Upjohn Company, Kalamazoo, Mich.

[21] Appl. No.: 81,583

[22] Filed: Aug. 3, 1987

Related U.S. Application Data

[63] Continuation of Ser. No. 761,239, Jul. 31, 1985, abandoned, which is a continuation-in-part of Ser. No. 653,999, Sep. 24, 1984, abandoned, and a continuation-in-part of Ser. No. 682,980, Dec. 18, 1984, abandoned.

[51] Int. Cl.$^4$ .......................................... C07D 401/12
[52] U.S. Cl. ..................... 546/271; 546/114; 546/115; 546/193; 546/148; 546/172; 546/174; 546/152; 544/131; 544/127; 544/128
[58] Field of Search ......................................... 546/271

[56] References Cited

U.S. PATENT DOCUMENTS

| | | | |
|---|---|---|---|
| 4,045,563 | 8/1977 | Berntsson et al. | 546/271 |
| 4,045,564 | 8/1977 | Berntsson et al. | 546/271 |
| 4,255,431 | 3/1981 | Junggren et al. | 546/271 |
| 4,337,257 | 6/1982 | Junggren et al. | 546/271 |
| 4,359,465 | 11/1982 | Ruwart | 546/271 |
| 4,575,554 | 3/1986 | Sih | 546/271 |

FOREIGN PATENT DOCUMENTS

| | | | |
|---|---|---|---|
| 1234058 | 6/1971 | United Kingdom . | |
| 2134523 | 8/1984 | United Kingdom | 546/271 |

*Primary Examiner*—Jane T. Fan
*Attorney, Agent, or Firm*—Lawrence T. Welch; Donald L. Corneglio

[57] ABSTRACT

The present invention provides novel N-substituted derivatives 2-(pyridylalkylenesulfinyl)benzimidazoles with gastric acid inhibiting effects.

3 Claims, No Drawings

N-SUBSTITUTED DERIVATIVES OF 2-(PYRIDYLALKENESULFINYL) BENZIMIDAZOLES AS GASTRIC ANTISECRETORY AGENTS

CROSS REFERENCE TO RELATED APPLICATIONS

This application is a continuation of 06/761,239, filed 31 July 1985, abandoned, which was a continuation-in-part of U.S. Ser. No. 06/653,999, filed 24 Sept. 1984, abandoned, and U.S. Ser. No. 06/682,980, filed 18 Dec. 1984, abandoned.

BACKGROUND OF THE INVENTION

The present invention involves novel compositions of matter. More particularly, the present invention involves novel N-substituted derivatives of 2-(pyridylalkylenesulfinyl)benzimidazoles which are useful as gastric antisecretory and cytoprotective agents.

Gastrointestinal inflammatory diseases are characterized by inflammation, specifically by the presence of edema, characteristic inflammatory cells (i.e., leucocytes, histiocytes, and macrophages), and, in some cases, necrosis and ulceration of the surface epithelium. These inflammatory diseases are known to be caused by a wide variety of agents present in the gastrointestinal tract which are known to attack the surfaces thereof, producing the inflammatory disease response. Such agents include micro-organisms (viruses and fungi), bacterial toxins, certain pharmaceutical agents (antibiotics and anti inflammatory steroids), and chemical agents (bile salts, toxic household chemicals). Gastric acid itself is also capable of attacking the stomach lining and producing an inflammatory state.

One means of preventing of treating certain gastrointestinal diseases, specifically gastric disease, is by the inhibition of gastric acid secretion. In situations where the integrity of the gastric mucosal barrier is compromised, gastric acid secretion can result in erosion of the epithelial cells with consequent inflammation and ulceration. Inhibition of such untoward gastric acid-induced effects can be achieved by the adminstration of a pharmacological agent effective to inhibit gastric secretion.

One class of such agents effective to inhibit gastric acid secretion are the gastric antisecretory prostaglandins. These substances are known to be effective in the treatment and care of gastric and duodenal ulcers as a result of the inhibition of gastric secretion. See, e.g., U.S. Pat. No. 3,903,297 (Robert, "Method of Treatment and Prophylaxis of Gastric Hypersecretion and Gastric Duodenal Ulcers Using Prostaglandin Analogs"), and Robert, "Antisecretory Property of Prostaglandins," Prostaglandin Symposium of the Worcester Foundation for Experimental Biology 16-17 Oct. 1967, Interscience, New York, page 47 (1978). Another important class of antisecretory agents are the histamine H2 receptor antagonists, including metiamide and most importantly cimetidine, N-cyano-N'-methyl-N"[2-[[(5-methyl-1H-imidazole-4-yl)methyl]thio]ethyl]guanidine. See, the Merck Index, 9th Edition, Appendix, page App-1 (1976), and Physician's Desk Reference, 36th Edition, 1812-1814 (1982).

Another means of treating such gastrointestinal diseases is through cytoprotection. Certain pharmacological agents have heretofore been known to be useful in exerting a cytoprotective effect on the gastrointestinal tract. This cytoprotective effect is manifest in the ability of such compounds to treat or prevent non-traumatically-induced, non-neoplastic inflammatory disease of the gastrointestinal tract. References describing such cytoprotective effects of prostaglandins are U.S. Pat. No. 4,083,998 (Robert, "Treatment of Inflammatory Diseases of the Mammalian Large Intestine with Cytoprotective Prostaglandins"), issued Apr. 11, 1978, U.S. Pat. No. 4,081,553 (Robert, "Cytoprotective Prostaglandins for Use in Intestinal Diseases"), issued Mar. 28, 1978, and U.S. Pat. No. 4,097,603 (Robert, "Gastric Cytoprotection with Non-Antisecretory Doses of Prostaglandins"), issued June 27, 1978. Gastric cytoprotection is a distinct pharmacological property which is unrelated to gastric anti secretory effects. See, e.g., Robert, U.S. Pat. No. 4,097,603, "Gastric Cytoprotection With Non-Antisecretory Doses of Prostaglandins," Robert, "Cytoprotection by Prostaglandins," Gastroenterology 77: 761-767 (1979), Robert, "Current History of Cytoprotection," Prostaglandins 21 (supp): 89 (1981), and Robert, et al., "Cytoprotection by Prostaglandins in Rats," Gastroenterology, 77: 433-443 (1979). Thus, compounds which are gastric anti-secretory agents may not be cytoprotective agents and vice-versa.

INFORMATION DISCLOSURE

U.S. Pat. No. 4,045,563 discloses certain substituted 2-[pyridylalkenylenesulfinyl]-benzimidazoles having gastric acid secretion inhibiting effects. U.S. Pat. Nos. 4,255,431 and 4,337,257 disclose certain 2-(2-benzimidazolyl)-pyridines which are useful in inhibiting gastric secretion. U.S. Pat. No. 4,359,465 discloses the cytoprotective use of certain heterocyclyalkylsulfinyl-benzimidazoles. Copending applications Ser. No. 510,468, filed 1 July 1983, and Ser. No. 617,419, filed 5 June 1984, disclose certain substituted 2-[monoannelated(3,4-, 4,5-, and 5,6-)pyridylalkylenesulfinyl]benzimidazoles as antisecretory agents. Copending application Ser. No. 558,087, filed 5 Dec. 1983, and Ser. No. 648,118, filed 6 Sept. 1984, disclose substituted 2-pyridylmethyl-thio and sulfinyl benzimidazoles as gastric antisecretory agents. Published British patent application 2,134,523 discloses certain N-substituted pyridylalkyl benzimidazoles.

SUMMARY OF THE INVENTION

The present invention particularly provides: a compound of the formula I,
wherein X is
(a) =S, or
(b) =SO;
wherein A and B are the same or different and are:
(a) hydrogen,
(b) —$R_1$,
(c) —$OR_1$,
(d) —$CF_3$,
(e) —$COR_1$, or
(f) —$CO_2R_1$;
wherein $R_1$ is ($C_1$–$C_4$)alkyl;
wherein D is a substituent of the Formula II, III, IV, or V,
wherein $R_3$, $R_4$ and $R_{10}$ are the same or different and are
(a) hydrogen, or
(b) ($C_1$–$C_4$)alkyl;
wherein m is 0 or 1
wherein $R_2$ is
(a) —$SR_5$, (b) —OR$_5$,
(c) —N(R$_4$)$_2$,
(d) 1-piperidinyl,
(e) 4-morpholinyl,
(f) 1-pyrrolidinyl,
(g) chloro,
(h) bromo, or
(i) fluoro;
wherein R$_5$ is
(a) (C$_1$-C$_4$)alkyl,
(b) (C$_2$-C$_2$)alkenyl,
(c) (C$_3$-C$_6$)cycloalkyl,
(d) —CH$_2$—PhX; or
(e) PhX;
wherein PhX is phenyl substituted by zero to 3 of the following:
(a) (C$_1$-C$_4$)alkyl,
(b) chloro,
(c) bromo,
(d) fluoro,
(e) nitro,
(f) CF$_3$, or
(g) OR$_3$;
wherein n is 0 or 1; and
wherein V is
(a) =CH$_2$,
(b) =O, or
(c) =S;
wherein G is
(a) hydrogen,
(b) (C$_1$-C$_4$)alkyl
(c) —COR$_6$,
(d) —COPhX,
(e) —CO(CH$_2$)$_m$CO$_2$R$_3$,
(f) —COCH$_2$PhX, or
(g) —C(O)—O—R$_{11}$;
wherein R$_6$ is
(a) (C$_1$-C$_{10}$)alkyl, or
(b) —AA;
wherein —AA is
(a) —(CH$_2$)$_p$—CH(NH$_2$)-R$_9$, or
(b) a side chain of amino acid,
wherein R$_9$ is
(a) hydrogen, or
(b) (C$_1$-C$_9$)alkyl;
wherein R$_{11}$ is
(a) (C$_1$-C$_{12}$)alkyl,
(b) (C$_2$-C$_{12}$)alkenyl,
(c) —PhX,
(d) —CH$_2$PhX,
(e) (C$_1$-C$_6$)cycloalkyl,
(f) —CH$_2$—(C$_1$-C$_6$)cycloalkyl, or
(g) (C$_1$-C$_6$)alkyl substituted by one more bromo or chloro groups;
wherein p is an integer from 1 to 9, inclusive: with the following provisos

(1) that the total number of carbon atoms in —(CH$_2$)$_p$— and R$_9$ are less than or equal to 9;
(2) m is zero only when G is —C(O)—O—R$_{11}$; and
(3) G is —C(O)—O—R$_{11}$ only when R$_2$ of Formula II is not —OR$_5$, or V in Formulas II, III or IV is =S.

The present invention further provides:
(1) A process for preparing a compound of Formula I, wherein G is —COR$_6$, —COPhX, —CO(CH$_2$)$_m$CO$_2$R$_3$, or —COCH$_2$PhX; which comprises: treating a compound of the Formula A-2 with:

(a) an acid anhydride containing the moiety —COR$_6$, —COPhX —CO(CH$_2$)$_m$CO$_2$R$_3$, or —COCH$_2$PhX, and a catalytic amount of N,N-dimethylaminopyridine, or (b) an activated acid containing the moiety —COR$_6$, —COPhX, —CO(CH$_2$)$_m$—CO$_2$R$_3$, or —COCH$_2$PhX;

(2) A process for preparing a compound of the Formula I, wherein G is —C(O)—O—R$_{11}$ and m is zero, which comprises:

(a) treating a compound of the formula B-1 with sodium hydride, and, subsequently, (b) treating the anion thus formed with a compound of the formula ClCOOR$_{11}$;

(3) A process for preparing a compound of the Formula I, wherein G is (C$_1$-C$_4$)alkyl, which comprises:

(a) treating a compound of the Formula C-1 with sodium hydride and, subsequently, (b) treating the anion thus formed with a compound of the formula CH$_3$CHXCOR$_{12}$, wherein X is chloro or bromo and R$_{12}$ is C$_1$-C$_4$alkyl; and (4) A process for preparing a compound of the Formula I, wherein G is —COR$_6$, —COPhX, —CO(CH$_2$)$_m$CO$_2$R$_3$, or COCH$_2$PhX, which comprises treatment of a compound of the Formula D-1 with a compound of the formula CH$_3$—CHX—O—C(O)—R$_{13}$, wherein X is chloro or bromo and R$_{13}$ is R$_6$, PhX, —(CH$_2$)$_m$—CO$_2$R$_3$, or —CH$_2$PhX.

The carbon atom content of various hydrocarbon-containing moieties is indicated by a prefix designating the minimum and maximum number of carbon atoms in the moeity, i.e., the prefix (C$_i$-C$_j$) indicates a moiety of the integer "i" to the integer "j" carbon atoms, inclusive. Thus (C$_1$-C$_{10}$) alkyl refers to alkyl of one to 4 carbon atoms, inclusive, or methyl, ethyl, propyl, butyl, pentyl, hexyl, heptyl, octyl, nonyl, decyl, and isomeric forms thereof.

Examples of (C$_3$-C$_{10}$)cycloalkyl which include alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methycyclobutyl, 3-propylcyclobutyl, 2,3,4-triethylcyclobutyl, cyclopentyl, 2,2-dimethylcyclopenyl, 2-pentylcyclopentyl, 3-tert-butylcyclopentyl, 2,2-dimethylcyclohexyl, cycloheptyl, cyclooctyl, cyclononyl and cyclodecyl.

Examples of C2-C4)alkenyl include 1-propenyl, 3-butenyl and isomeric forms thereof.

Examples of PHX include phenyl, (o-, m-, p-)tolyl, (o-, m-, p-)ethylphenyl, 2-ethyl-tolyl, 4-ethyl-o-tolyl, 5-ethyl-m-tolyl, (o-, m-, or p-)propylpheny, 2-propyl-(o-,m-, or p-)tolyl, 4-isopropyl-2,6-xylyl, 3-propyl-4-ethyl-phenyl, (2,3,4-, 2,3,6-, or b 2,4,5-)trimethylphenyl, (o-, m-, or p-)fluorophenyl, (o-, m-, or p-trifluoromethyl)-phenyl, 4-fluoro-2,5-xylyl, (2,4-, 2,5-, 2,6-, 3,4-, or 3,5-)difluorophenyl, (o-, m-, or p-)chloropenyl, 2-chloro-p-tolyl, (3-, 4-, 5-, or 6-)chloro-o-tolyl, 4-chloro-2-propyl-phenyl, 2-isopropyl-4-chlorophenyl, 4-chloro-3,5-xylyl, (2,3-, 2,4-, 2,5-, 2,6-, or 3,5-)dichlorophenyl, 4-chloro-3-fluorophenyl, (3- or 4-)chloro-2-fluorophenyl, (o-, m-, or p-)trifluoromethylphenyl, (o-, m-, or p-)ethoxyphenyl, (4- or 5-)chloro-2-methoxyphenyl, and 2,4-dichloro-(5- or 6-)methylphenyl.

Pharmaceutically acceptable acid addition salts are formed when G contains an amine moiety. These salts include hydrochloride, hydrobromide, hydroiodide, sulfate, phosphate, acetate, propionate, lactate, maleate, malate, succinae, tartrate, and the like. They are prepared by methods well known in the art.

By "side chain of an amino acid" is meant the dehydroxylated form of such acids including the naturally occurring acids such as: glycine, alanine, valine, leucine, isoleucine, phenylalanine, lysine, proline, tryptophan, methionine, serine, threonine, cysteine, tyrosine, asparagine, glutamine, aspartic acid, glutamic acid, arginine, ornithine, and histidine, and synthetic derivatives thereof. These compounds may be in L or D configuration and are well known and readily available to those skilled in the art.

The compounds of the present invention may also be in the form of pharmacologically acceptable salts. These salts are formed when at least one of A and B is $CO_2M$ (with M being a pharmacologically acceptable cation). Such cations include: pharmacologically acceptable metal cations, ammonium, amine cations, or quaternary ammonium cations.

Especially preferred metal cations are those derived from the alkali metals, e.g., lithium, sodium, and potassium, and from the alkaline earth metals, e.g., magnesium and calcium, although cationic forms of other metals, e.g., aluminum, zinc, and iron are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, a-phenylethylamine, b-phenylethylamine, ethylenediamine, diethylenetriamine, and the like aliphatic, cycloaliphatic, araliphatic amines containing up to and including about 18 carbon atoms, as well as heterocyclic amines, e.g., piperidine, morpholine, pyrrolidine, piperazine, and lower-alkyl derivatives thereof, e.g.,
1-methylpiperidine,
4-ethylmorpholine,
1-isopropylpyrrolidine,
2-methylpyrrolidone,
1,4-dimethylpiperazine,
2-methylpiperidine,
and the like, as well as amines containing water-solubilizing or hydrophilic groups, e.g.,
mono-, di-, and triethanolamine,
ethyldiethanolamine,
N-butylethanolamine,
2-amino-1-butanol,
2amino-2-ethyl-1,3-propanediol,
2-amino-2-methyl-1-propanol,
tris(hydroxymethyl)aminomethane,
N-phenylethanolamine,
N-(p-tert-amylphenyl)diethanolamine,
galactamine,
N-methylglycamine,
N-methylglucosamine,
ephedrine,
phenylephrine,
epinephrine,
procaine,
and the like. Further useful amine salts are the basic amino acid salts, e.g.,
lysine and
arginine.

Examples of suitable pharmacologically acceptable quaternary ammonium cations are
tetramethylammonium,
tetraethylammonium,
benzyltrimethylammonium,
phenyltriethylammonium, and the like.

The compounds of the present invention will be named herein using the Chemical Abstracts numbering system (see Naming and Indexing of Chemical Substances for Chemical Abstracts during the Ninth Collective Period (1972–1976), a reprint of section IV from the Volume 76 Index Guide.)

Surprisingly and unexpectedly, the compounds of the present invention are chemically more stable than the benzimidazoles from which they are derived. They are particularly more stable in acid conditions, such as in the stomach. They are also more soluble in water, providing an improved means for pharmaceutical formulation. Further, these compounds retain strong antisecretory activity when administered subcutaneously and are generally more potent than the parent benzimidazoles when administered orally.

Compounds of this invention have been tested in one or more standard laboratory tests which demonstrate gastric antisecretory activity. In a test for in vivo inactivation of $(H+-K+)$ATP-ase in the rat, 2-(((4-methoxy-3,5-dimethyl-2-pyridinyl)methyl)-sulfinyl)-benzimidazole, acetate (ester) (compound 6 of Table I) was shown to be the most effective, having an $ED_{50}$ of 1 mg/kg when administered subcutaneously. Further, certain of these compounds have been shown to retain their high potency as inhibitors of gastric acid secretion in rats when administered orally. In this test system one compound was found to be the most effective during oral administration. 2-((2-Pyridinylmethyl)-sulfinyl)-1H-benzimidazole-1-methanol, acetate (ester) (compound 1 of Table I) exhibited an $ED_{50}$ in the rat gastric antisecretory assay, administered orally, of 5 mg/kg, which is the same $ED_{50}$ exhibited by this compound during subcutaneous administration.

In the test for in vivo inactivation of $(H^+-K^+)$ATPase in the rat, 2-[(4-ethylthio-3-methyl-2-pyridinylmethyl)sulfinyl]-1H-benzimidazole-1-carboethoxy ester; 2-[(4-ethylthio-3-methyl-2-pyridinylmethyl)sulfinyl]-1H-benzimidazole-1-carbophenoxy ester; and 2-[(4-ethylthio-3-methyl-2-pyridinylmethyl)sulfinyl]-1θ-benzimidazole-1-carbo-p-nitrobenzyloxy ester were shown to be effective, having $ED_{50}$'s of between 5 and 10 mg/kg when administered subcutaneously. Further, certain of the compounds of this invention were shown to be effective in a standard laboratory test for gastric acid secretion in isolated rabbit glands. The two compounds that were the most effective as inhibitors of gastric acid secretion in this test were 2-[(4-ethylthio-3-methyl-2-pyridinylmethyl)-sulfinyl]-1H-benzimidazole-1-carboisobutyloxy ester and 2-[(4-ethylthio-3-methyl-2-pyridinylmethyl)sulfinyl]-1H-benzimidazole-1-carbovinyloxy ester. Both of these compounds exhibited $ID_{50}$'s of 10 mg/kg in this test.

In general, the preferred compounds of this invention are those of the formula I wherein A and B are hydrogen, X is =SO, D is a substituent of the formula II (wherein V is =S) or V (wherein $R_2$ is alkylthio), and G is —$(C_1-C_4)$alkyl or —$COR_6$.

All of the compounds of this invention are useful as gastric antisecretory agents.

Compounds of this invention are administered for gastric antisecretory purposes orally, parenterally, (e.g., intravenously, subcutaneously, intramuscularly or intraparenterally), rectally, or vaginally in forms such as pills, capsules, solutions, suspensions, suppositories, or bougies. The compounds of this invention are formulated into these pharmaceutical compositions by means known to the pharmaceutical art.

An ordinarily skilled physician can readily determine persons suffering from gastrointestinal diseases characterized by the gastric-acid induced effects noted above. These conditions are treated using the compounds of the present invention.

Typical dose ranges for the compounds of this invention range from about 0.01 µg per kg to about 250 mg per kg, preferably from about 0.1 to 100 mg per kg. The choice of the use, route, and frequency of administration of the compounds of this invention depends on the weight, age, and gastrointestinal disease of the patient and the particular compound employed. These decisions are readily made by a physician of ordinary skill in the art.

The compounds of this invention may also exert cytoprotective effects. If employed for this purpose, they could be administered as described, for example, in U.S. Pat. No. 4,359,465, particularly cols. 7 and 8 thereof. The doses employed for this purpose would in general be less than those used for gastric antisecretory effects.

The compounds of the present application are prepared by the methods of Charts A–D. In the Chart A, G is all of the definitions of G except hydrogen, $G_2$ is $(C_1-C_4)$alkyl, and all other variables are as defined above.

In Chart A, a benzimidazole compound of the Formula A-1 is hydroxymethylated by means known in the art, e.g., treatment with formaldehyde in acetonitrile (see Varma, et al., Eur. J. Med. Chem. 15: 536 (1980) and Haugwitz, et al., J. Med. Chem. 22: 1113 (1979)). The benzimidazole compounds of the Formula A-1 are known and/or can be prepared by the methods described U.S. Pat. Nos. 4,575,554; 4,045,563; 4,255,431; and 4,337,257; which patents are incorporated herein by reference.

The compounds of the present invention wherein G is hydrogen, $-COR_6$, $-COPhX$, $-CO(CH_2)_mCO_2R_3$, or $-COCH_2PhX$ are prepared as depicted in Chart A.

The Formula A-2 hydroxymethyl compound in pyridine is then treated at 20°–50° C., preferably at 25° C. with slightly more than one molar equivalent of the appropriate acid anhydride and a catalytic amount of N,N-dimethylaminopyridine or reacted in acetone at 20°–50° C. preferably at 25° C. with one molar equivalent of the appropriate activated acid (e.g., prepared in situ from an acid, isobutylchloroformate and triethylamine) for 1–2 hours to yield an ester of Formula A-3. The final product can be purified by silica gel chromatography using common organic solvents, such as ethyl acetate or ethyl acetate-hexane solvent mixtures for the eluent. The acids corresponding to G are well known and readily available to those skilled in the art and/or may be prepared by known means. When X is =S, this compound is then oxidized as described in the U.S. patents and applications noted above (e.g., using meta-chloroperbenozic acid) to yield the corresponding sulfoxide. When the acid used is an amino acid, the amino function is blocked by conventional means (e.g., using a tertiary butyloxy carbonyl group) prior to reaction with the Formula A-2 compound. Such protected amino acids are also commercially available. The blocking group is then removed by reaction with a pharmaceutically acceptable acid to form an acid addition salt. Thus, for example, the Formula A-2 hydroxy compound is reacted with the t-butyloxycarbonyl amino acid of the Formula A-2 in the following manner. The Formula A-2 compound and N,N-dimethylaminopyridine (DMAP) are dissolved in dry pyridine. Separately, dicylohexylcarbodiimide (DCCD) and a t-butyloxycarbonyl amino acid are dissolved in pyridine. These two pyridine solutions are slowly mixed together with continuous stirring. Dicyclohexylurea (DCHU) is formed as a by-product and is filtered off. After the solvent is evaporated, the compound of the Formula A-3 thus formed is reacted with an acid of the formula HX to yield the Formula A-4 compound.

Alternatively, the amino acid side chains within the scope of G may be added through a "mixed-anhydride" route. A t-butyloxycarbonyl amino acid and N-methylmorpholine are dissolved in dry tetrahydrofuran (THF). To this solution, isobutylchloroformate is added dropwise under a nitrogen atmosphere. After the precipitates which form are filtered off, a mixture of a compound of the Formula A-2 and dimethylaminopyridine (DMAP) in dry THF is added. After 60 minutes at room temperature, the reaction mixture is dried under vacuum. If necessary, the pure product is isolated by means of liquid chromatography. The final product is then prepared as described above.

The compounds of the present invention where m is zero and G is $-C(O)-O-R_{11}$ are prepared as described in Chart B. In Chart B, a benzimidazole compound of the Formula B-1 in dimethylformamide is treated at from 20°–50° C., preferably at 25° C. with one molar equivalent of sodium hydride. After stirring a few minutes at this temperature, the appropriate chloroformate reagent (slightly more than one molar equivalent) of the formula $ClCOOR_{11}$ is added to the benzimidazole aminon and the reation is allowed to proceed at from 20°–50° C., preferably at 25° C. for 15–30 minutes. A pure compound of the Formula B-2 is then isolated by silica gel chromatography (ethyl acetate or ethyl acetate-hexane solvent mixtures as eluents) and/or by crystallization from ethyl acetate or ethyl acetate-ether solvent mixtures.

The benzimidazole compounds of the Formula B-1 are known and/or can be prepared by the methods described in U.S. Pat. Nos. 4,045,563; 4,255,431; and 4,337,257; which patents are incorporated herein by reference, and in copending applications S.N. 617,419, filed 5 June 1984 (Appendix A) and S.N. 648,118 filed 6 Sept. 1984 (Appendix B). The chloroformates of the formula $ClC(O)-O-R_6$ are well known, readily available compounds and/or can be prepared by known methods.

In Chart C, a benzimidazole compound of the Formula C-1 in dimethylformamide is treated at from 20° to 50° C., preferably at 25° C. with one molar equivalent of sodium hydride. The resulting benzimidazole anion is then allowed to react with slightly one than one equivalent of a halo ether of the formula $CH_3CHX-O-R_{12}$, wherein X is chloro or bromo and $R_{12}$ is $C_1-C_4$alkyl, and the reaction is stirred at from 20°–50° C., preferably at 25° C. for 15–30 minutes. A pure compound of the Formula C-2 is then isolated by silica gel chromatography using ethylacetate-hexane solvent mixtures as the eluent and/or by direct crystallization from common organic solvents, such as ethyl acetate or ethyl acetate-ether solvent mixtures. The chloroalkyl alkyl ethers are commercially available or readily prepared by methods known to those skilled in the art.

Ester derivatives of the present invention wherein $R_{10}$ is other than hydrogen are prepared as depicted in Chart D. In Chart D, a benzimidazole compound of the Formula D-1 in acetonitrile is allowed to react at 25° C. with 2-3 equivalent of an appropriate α-haloalkyl ester. The α-haloalkyl esters can be obtained from the corresponding acyl halides and an aldehyde [see, L. H. Ulich and R. Adams, J. Am. Chem. Soc., 43, 660 (1921)]. For better yields in the reaction, the bromoalkyl esters are the more preferred α-haloalkyl ester reagents. Alternatively, the anion of benzimidazole of Formula D-1 can be formed using the sodium hydride procedure described previously and treated with α-haloalkyl esters. By the above procedures there is obtained a compound of the Formula D-2 which is oxidized in chloroform at 0°-5° C. with m-chloroperbenzoic acid to give a compound of Formula D-3. The final product is then purified by silica gel chromatography using preferably ethyl acetate or ethyl acetate-hexane solvent mixtures as the eluent.

All of the compounds of this invention are prepared by the procedures described above.

DESCRIPTION OF THE PREFERRED EMBODIMENTS

The present invention is seen more fully by the examples given below.

EXAMPLE 1

2-[(2-Pyridinylmethyl)sulfinyl]-1H-benzimidazole-1-methanol (Formula I: A and B are hydrogen, D is a Formula V substituent, $R_2$, $R_3$, and $R_4$ are hydrogen, X is =S, G is hydrogen)

Refer to Chart A (conversion of A-1 to A-2).

To a solution of 10 g (41.45 mmol) of 2-(2-pyridinyl)-methylthiobenzimidazole in 220 ml of acetonitrile is added 5.00 ml of 37% formaldehyde solution dissolved in 10 ml of acetonitrile. After addition, the mixture is heated in an oil bath maintained at 70° C. for 15 minutes. At the end of this time, the major portion of the solvent is removed in vacuo, the residue diluted with chloroform, the chloroform solution washed with water, saturated brine and dried through anhydrous $Na_2SO_4$. Removal of the solvent in vacuo gives the crude product which is recrystallized from ethyl acetate-ether-Skellysolve B (30:25:15) to give 9.687 g of the title compound, with a melting point of 80°-83° C.

Anal. Calcd. for $C_{14}H_{13}N_3PS$: C, 61.99; H, 4.80; N, 15.50; S, 11.81. Found: C, 62.22; H, 4.96; N, 15.64; S, 11.88.

NMR ($CDCl_3$, δ) 8.50, 7.80-7.10, 5.70, 4.40.

Mass spectrum M+271. Found 242 (M+-HCHO+H).

TLC Rf 0.22 in chloroform-acetone (3:1).

Example 2

2-[(4-Methoxy-3,5-dimethyl-2-pyridinylmethyl)-thio]-1H-benzimidazole-1-methanol (Formula I: A and B are hydrogen, D is a Formula V substituent, $R_2$ is methoxy, $R_3$ and $R_4$ are methyl, X is =S, G is hydrogen)

Refer to Chart A (conversion of A-1 to A-2).

Following the procedure described in Example 1, 1.63 g (5.45 mmol) of the thioether corresponding to the titled compound gives 1.44 g of the title compound, mp 162°-165° C.

Mass spectrum calcd. for $C_{17}H_{19}N_3O_2S$: No (M+H) at 330. Found 300 (M+-HCHO). NMR ($CDCl_3$, δ) 8.00, 7.80-27.20, 5.80, 4.50, 3.80, 2.35, 2.20.

TLC Rf 0.24 in methylene chloride-acetone (6:1).

EXAMPLE 3

2-[(4-Ethylthio-3-methyl-2-pyridinylmethyl)thio]-1H-benzimidazole-1-methanol

Refer to Chart A (conversion of A-1 to A-2).

To a magnetically stirred suspension of 2-[(4-ethylthio-3-methyl-2-pyridinylmethyl)thio]-benzimidazole (0.787 g, 2.50 mmol) in 30 ml of acetonitrile was added 0.36 ml of 37% formaldehyde solution. The mixture was heated in a 65° C. oil both for 15 min and worked up in the same manner as previously described to afford the title compound.

NMR ($CDCl_3$, δ) 8.10 (d, 1H, J=5 HZ), 7.70-6.90 (m, 5H), 5.70 (S, 2H), 4.5-0 (S, 2H), 2.85 (q, 2H, J=7 HZ), 2.25 (S, 3H), 1.35 (t, 3H, J"7 HZO.

TLC Rf 0.40 in ethyl acetate-Skellysolve B (2:1).

EXAMPLE 4

2-[3,4-dihydro-2H-thieno(2,3-c)pyridinylmethyl)thio]-1H-benzimidazole-1-methanol (Formula I: A and B are hydrogen, D is a Formula II substituent, n is 1, V is =S, X is =S, G is hydrogen)

Refer to Chart A (conversion of A-1 to A-2).

Following the procedure previously described in Example 3, 0.300 g (0.96 mmol) of thioether gives 0.322 g of N-hydroxymethyl product.

NMR ($CDCl_3$, δ) 7.95, 7.85-6.90, 5.80, 4.50, 2.90, 2.10.

TLC Rf 0.43 in chloroform-acetone (3:1).

EXAMPLE 5

2-[(4-Chloro-3-methyl-2-pyridinylmethyl)thio]-1H-benzimidazole-1-methanol (Formula I: A and B are hydrogen, D is a Formula V substituent, G is hydrogen, X is =S, $R_3$ is methyl, $R_2$ is chloro, $R_4$ is hydrogen)

Refer to Chart A (conversion of A-1 to A-2).

Following the procedure previously described in Example 3, 2.50 g (8.65 mmol) of thioether afforded 2.35 g of the product as a white crystalline solid. NMR ($CDCl_3$-$CD_3OD$, δ) 8.25, 7.80-7.20, 5.80, 4.80, 2.60.

TLC Rf 0.35 in Skellysolve-acetone (2:1).

EXAMPLE 6

2-[(4-Ethylthio-3-methyl-2-pyridinylmethyl)sulfinyl]-1H-benzimidazole-1-methanol (Formula I: A and B are hydrogen, D is a Formula V substituent, G is hydrogen, X is =SO, $R_3$ is methyl, $R_2$ is ethylthio, $R_4$ is hydrogen)

Refer to Chart A (conversion of A-1 to A-2).

To a magnetically stirred suspension of 2-[(4-ethylthio-3-methyl-2-pyridinylmethyl)suflinyl]-benzimidazole (1.00 g, 3.02 mmol) in 55 ml of acetonitrile is added in one portion 1.13 ml of 37% formaldehyde solution and the mixture heated in an 65° C. oil bath. Heating is continued for 10 min. The acetonitrile was then removed in vacuo and the resulting dark residue was used without further purification in the subsequent reactions.

NMR ($CDCl_3$, δ) 8.10, 7.90-6.95, 5.95, 4.85, 2.70, 2.25, 1.13.

TLC Rf 0.33 in acetone-Skellysolve B (1:1).

EXAMPLE 7

2-[(4-Ethylthio-3-methyl-2-pyridinylmethyl)sulfinyl]-1H-benzimidazole-1-methanol, acetate (ester)

(Formula I: A and B are hydrogen, D is a Formula V substituent, G is hydrogen, X is =SO, $R_3$ is methyl, $R_2$ is ethylthio, $R_4$ is hydrogen)

Refer to Chart A (conversion of A-1 to A-2).

To a magnetically stirred solution of N-hydroxymethyl (1.09 g, 3.02 mmol) in 25 ml of pyridine is added 8 ml of acetic anhydride and 150 mg of 4-N,N-dimethylaminopyridine. Stirring was continued at 25° C. for 1.5 hr. The reaction was worked up as described previously. The crude product is chromatographed with silica gel and eluted with ethyl acetate to afford 0.768 g of an oil which slowly crystallized. Recrystallization with ethyl acetate-ether-Skellysolve B yielded 0.591 g of product, mp 132°–133° C.

TLC Rf 0.38 in ethyl acetate.

See Table I for physical constants.

EXAMPLE 8

2-[(4-Methoxy-3,5-dimethyl)-2-pyridinylmethyl)thio-1H-benzimidazole-1-methanol, acetate (ester)

(Formula I: A and B are hydrogen, D is a Formula V substituent, X is =S, G is $CH_3$—C(O)—, $R_3$ and $R_4$ are methyl, and $R_2$ is methoxy)

Refer to Chart A (conversion of A-2 to A-3).

To a magnetically stirred solution of N-hydroxymethyl thioether (1.30 g, 3.95 mmol) in 25 ml of pyridine was added 6 ml of acetic anhydride and 40 mg of 4-N,N-dimethylaminopyridine. Stirring was continued at 25° C. for 1 hour. At the end of this period, the solution was poured onto crushed ice and water. The resulting white solid was filtered with suction and dried under vacuum at 55° C. to give 1.29 g of the title compound.

NMR (CDCl$_3$, δ)) 8.27, 7.90–7.20, 6.15, 4.85, 3.80, 3.32, 2.20, 2.02.

Mass spectrum Calcd. for $C_{19}H_{22}N_3O_3S$: 372.1382. Found: 372.1379.

TLC Rf 0.35 in Skellysolve B-acetone (2:1).

EXAMPLE 9

2-[(2-Pyridinylmethyl)thio]-1H-benzimidazole-1-methanol, acetate (ester)

(Formula I: A and B are hydrogen, D is a Formula V substituent, X is =S, G is $CH_3$—C(O)—, $R_2$, $R_3$ and $R_4$ are methyl)

Refer to Chart A (conversion of A-2 to A-3).

Following the procedure described for the preparation of Example 8, 5.00 g (18.45 mmol) of N-hydroxymethyl thioether yielded 5.75 g of the title compound as viscous oil.

NMR (CDCl$_3$, δ) 8.60, 7.80–7.13, 6.10, 4.80, 2.03.

Mass spectrum calcd. for $C_{16}H_{16}N_3O_2S$: 314.0963. Found: 314.0940.

TLC Rf 0.43 in Skellysolve B-acetone (1:1).

EXAMPLE 10

2-[(4-Ethylthio-3-methyl-2-pyridinylmethyl)thio]-1H-benzimidazole-1-methanol, acetate (ester)

(Formula I: A and B are hydrogen, D is a Formula V substituent, X is =S, G is $CH_3C(O)$—, $R_3$ is methyl, $R_2$ is ethylthio, and $R_4$ is hydrogen)

Refer to Chart A (conversion of A-2 to A-3).

Following the procedure described for Example 8, 1.860 g (5.39 mmol) of N-hydroxymethyl thioether afforded 1.936 g of the title compound as a low melting white crystalline solid.

NMR (CDCl$_3$, δ) 8.32, 7.95–7.20, 7.05, 6.10, 4.80, 2.95, 2.30, 2.03, 1.40.

TLC Rf 0.38 in methylene chloride-acetone (4:1).

EXAMPLE 11

2-[(3,4-Dihydro-2H-thieno(3,2-c)pyridinylmethyl)-thio]-1H-benzimidazole-1-methanol, acetate (ester)

(Formula I: A and B are hydrogen, D is a Formula II substituent, n is 1, V is =S, X is =S, G is $CH_3C(O)$—)

Refer to Chart A (conversion of A-2 to A-3).

Following the acetylation conditions described previously in Example 8, 0.322 g (0.94 mmol) of N-hydroxymethyl compound yielded 0.330 g of product after silica chromatography with methylene chloride-acetone (8:1).

NMR (CDCl$_3$, δ) 8.20, 7.90–7.25, 7.03, 6.15, 4.80, 3.00, 2.10, 2.03.

TLC Rf 0.34 in methylene chloride-acetone (6:1).

EXAMPLE 12

2-[(4-Chloro-3-methyl-2-pyridinylmethyl)thio]-1H-benzimidazole-1-methanol, acetate (ester)

(Formula I: A and B are hydrogen, D is a Formula V substituent, G is $CH_3C(O)$—, X is =S, $R_3$ is methyl, $R_2$ is chloro, $R_4$ is hydrogen)

Refer to Chart A (conversion of A-2 to A-3).

Following the acetylation conditions previously described in Example 8, 2.35 g (7.37 mmol) of N-hydroxymethyl compound gave, after recrystallization from ethyl acetate-ether, 2.34 g of product.

NMR (CDCl$_3$, δ) 8.40, 7.85–7.25, 6.15, 4.90, 2.55, 2.03.

TLC Rf 0.48 in Skellysolve B-acetone (2:1).

EXAMPLE 13

2-[(2-Pyridinylmethyl)thio]-1H-benzimidazole-1-methanol, methyl succinate (ester)

(Formula I: A and B are hydrogen, D is a Formula V substituent, X is =S, G is $CH_3CO_2(CH_2)_2$—C(O)—, $R_2$, $R_3$, and $R_4$ are hydrogen)

Refer to Chart A (conversion of A-2 to A-3).

To a magnetically stirred solution of N-hydroxymethyl thioether (1.084 g, 4.0 mmol) in 12 ml of pyridine is added 0.600 g (6.0 mmol) of succinic anhydride and 10–15 mg of 4-N,N-dimethylaminopyridine. Stirring is continued at 25° C. for 17 hours. At the end of this time, the reaction is diluted with water, and extracted with chloroform. The chloroform solution is washed with saturated brine, dried and concentrated in vacuo. The residual oil is dissolved in methanol-ether (5:1) and treated with ethereal diazomethane. The solvents are then removed in vacuo and the crude product chromatographed with ethyl acetate to afford 1.425 g of product as a colorless oil.

NMR (CDCl$_3$, δ) 8.55, 7.75–7.20, 6.08, 4.85, 3.55, 2.55.

TLC Rf 0.47 in ethyl acetate.

EXAMPLE 14

2-[(2-Pyridinylmethyl)thio]-1H-benzimidazole-1-methanol, octanoate (ester)

(Formula I: A and B are hydrogen, D is a Formula V substituent, X is =S, G is $CH_3$—$(CH_2)_6$—$C(O)$—, $R_2$, $R_3$ and $R_4$ are hydrogen)

Refer to Chart A (conversion of A-2 to A-3).

To a magnetically stirred solution of octanoic acid (0.864 g, 6.0 mmol) in 50 ml of acetone is added triethylamine (1.25 ml, 9.0 mmol) and isobutylchloroformate (1.16 ml, 9.0 mmol). The contents are stirred at 25° C. for 15 min. At the end of this time, N-hydroxymethyl thioether (1.084 g, 4.0 mmol), is dissolved in 10 ml of pyridine, is added and the reaction stirred at 25° C. for 75 min. The reaction is then diluted with 300 ml of chloroform, washed with 125 ml of water, 100 ml of saturated sodium bicarbonate, saturated brine, dried and concentrated in vacuo to yield the crude product. Silica chromatography with Skellysolve B-ethyl acetate (1:1) afforded 0.838 g of product as a viscous colorless oil.

NMR ($CDCl_3$, $\delta$) 8.60, 7.80–7.10, 6.10, 4.80, 2.25, 1.85–1.10, 0.88.

TLC Rf 0.43 in ethyl acetate-Skellysolve B (2:1).

EXAMPLE 15

2-[(2-Pyridinylmethyl)thio]-1H-benzimidazole-1-methanol, isobutylate (ester)

(Formula I: A and B are hydrogen, D is a Formula V substituent, X is =S, $(CH_3)_2CH$—$C(O)$, $R_2$, $R_3$, and $R_4$ are hydrogen)

Refer to Chart A (conversion of A-2 to A-3).

To a magnetically stirred solution of N-hydroxymethyl thioether (0.750 g, 2.76 mmol) in 20 ml of methylene chloride was added 0.40 ml (2.80 mmol) of thiethylamine and 0.39 ml (3.00 mmol) of isobutylchloroformate. Stirring was combined at 25° C. for 1.5 hour, the reaction diluted with 300 ml of chloroform, the chloroform solution washed with saturated sodium bicarbonate, saturated brine, and dried through anhydrous sodium sulfate. Removal of the solvent in vacuo gave 1.107 g of a semi-solid orange oil. This crude product was then used without further purification.

TLC Rf 0.40 in ethyl acetate-Skellysolve B (2:1).

EXAMPLE 16

2-[(2-Pyridinylmethyl)thio]-1H-benzimidazole-1-methanol, isopropionate (ester)

(Formula I: A and B are hydrogen, D is a Formula V substituent, X is =S, G is $(CH_3)_2CH$—$C(O)$—, $R_2$, $R_3$, and $R_4$ are hydrogen)

Refer to Chart A (conversion of A-2 to A-3).

Following the same procedure described for the preparation of Example 2, 0.750 g (2.76 mmol) of N-hydroxymethyl thioether, or isobutyric acid 0.264 g (3.00 mmol of isobutylchloroformate 0.39 ml (3.00 mmol) and 0.42 ml (3.00 mmol) of triethylamine afforded 0.53 g of product as a viscous oil.

NMR ($CDCl_3$, $\delta$) 8.60, 7.80–7.05, 6.05, 4.80, 2.50, 1.10.

TLC Rf 0.38 in ethyl acetate-Skellysolve B (2:1).

EXAMPLE 17

2-[(4-Ethylthio-3-methyl-2-pyridinylmethyl)sulfinyl]-1H-benzimidazole-1-carboethoxy ester (Formula I: A and B are hydrogen, D is a Formula V substituent, $R_3$ is methyl, $R_2$ is ethylthio, $R_4$ is hydrogen, $X_1$ is =SO, G is —$C(O)$—O—$CH_2CH_3$)

To a magnetically stirred suspension of 60% oil dispersion sodium hydride (0.067 g, 1.66 mmol) in dimethylformamide (10 ml) was added 0.500 g (1.51 mmol) of 2-[(4-ethylthio-3-methyl-2-pyridinylmethyl)-sulfinyl]-1H-benzimidazole and 0.196 g (1.81 mmol) of ethyl chloroformate. Stirring was continued at room temperature for 30 min. The reaction was then diluted with 500 ml of ethyl acetate-ether (2:3 v/v), washed with water, saturated brine and the organic solvent is dried over anhydrous sodium sulfate. Concentration of the solvent in vacuo gave the crude product which was chloride-acetone (4:1 v/v), the homogeneous fractions combined, the solvent evaporated, and the resulting solid recrystallized from ethyl acetate-ether-Skellysolve B to provide 0.350 g of the title compound as a tan solid, mp 135°–136° C. (dec.).

Anal. Calc'd. for $C_{19}H_{21}N_3O_3S_2$: C, 56.58; H, 5.21; N, 10.42; S, 15.88. Found: C, 56.22; H, 5.32; N, 10.30; S, 15.55.

EXAMPLE 18

2-[(Ethylthio-3-methyl-2-pyridinylmethyl)sulfinyl]-1H-benzimidazole-1-carboisobutyloxy ester (Formula I: A and B are hydrogen, D is a Formula V substituent, $R_3$ is methyl, $R_2$ is ethylthio, $R_4$ is hydrogen, $X_1$ is =SO, G is —$C(O)$—O—$CH_2CH(CH_3)_2$)

Following the same procedure described in Example 1, 0.500 (1.51 mmol) of 2-[(4-ethylthio-3-methyl-2-pyridinylmethyl)sulfinyl]-1H-benzimidazole and 0.411 g (3.02 mmol) of isobutyl chloroformate gave 0.362 g of the title compound, mp 85°–91° C.

Anal. Calc'd. for $C_{21}H_{25}N_3O_3S_2$: C, 58.47; H, 5.80; N, 9.74; S, 14.85. Found: C, 57.80; H, 5.83; N, 9.58; S, 14.99.

EXAMPLE 19

2-[(4-Ethylthio-3-methyl-2-pyridinylmethyl)sulfinyl]-1H-benzimidazole-1-carbobenzyloxy (Formula I: A and B are hydrogen, D is a Formula V substituent, $R_3$ is methyl, $R_2$ is ethylthio, $R_4$ is hydrogen, $X_1$ is =SO, G is —$C(O)$—O—$CH_2PhX$ and PhX is phenyl)

Following the same procedure described in Example 1, 0.500 g (1.51 mmol) of 2-[(4-ethylthio-3-methyl-2-pyridinylmethyl)sulfinyl]-1H-benzimidazole and 0.310 g (1.81 mmol) of benzyl chloroformate afforded 0.444 g of the title compound as a white crystalline solid, mp 156°–157° C. (dec).

Anal. Calc'd. for $C_{24}H_{23}N_3O_3S_2$: C, 61.94; H, 4.95; N, 9.03; S, 13.76. Found: C, 61.54; H, 5.03; N, 8.95; S, 13.56.

EXAMPLE 20

2-[(4-Ethylthio-3-methyl-2-pyridinylmethyl)sulfinyl]-1H-benzimidazole-1-carbophenoxy ester (Formula I: A and B are hydrogen, D is a Formula V substituent, $R_3$ is methyl, $R_2$ is ethylthio, $R_4$ is hydrogen, $X_1$ is =SO, G is —$C(O)$—$CH_2Phx$ and PhX is phenyl)

Following the procedure described in Example 1, 0.500 g (1.51 mmol) of 2-[(4-ethylthio-3-methyl-2-pyridinylmethyl)sulfinyl]-1H-benzimidazole and 0.283 g (1.81 mmol) of phenyl chloroformate yielded 0.293 g of the title compound as a buff colored crystalline solid, mp 136°–137° C. (dec).

Anal. Calc'd. for $C_{23}H_{21}N_3O_2S_2$: C, 61.20; H, 4.66; N, 9.31; S, 14.19. Found: C, 60.77; H, 4.72; N, 9.38; S, 14.33.

EXAMPLE 21

2-[(4-Ethylthio-3-methyl-2-pyridinylmethyl)sulfinyl]-1H-benzimidazole-1-carbo-p-nitro-benzyloxy ester (Formula I: A and B are hydrogen, D is a Formula V substituent, $R_3$ is methyl, $R_2$ is ethylthio, $R_4$ is hydrogen, $X_1$ is =SO, Y is —C(O)—O—CH$_2$PhX and PhX is p-nitro-phenyl)

Following the procedure described in Example 1, 0.500 g (1.51 mmol) of 2-[(4-ethylthio-3-methyl-2-pyridinylmethyl)sulfinyl]-1H-benzimidazole and 0.390 g (181 mmol) of p-nitrobenzyl chloroformate gave 0.409 g of the title compound as a buff-colored crystalline solid, mp 152°–153° C. (dec).

Anal. Calc'd. for $C_{24}H_{22}N_4O_5S_2$: C, 56.47; H, 4.31; N, 10.98; S, 12.55. Found: C, 56.36; H, 4.34; N, 10.91; S, 12.45.

EXAMPLE 22

2-[(4-Ethylthio-3-methyl-2-pyridinylmethyl)sulfinyl]-1H-benzimidazole-1-carbovinyloxy ester (Formula I: A and B are hydrogen, D is a Formula V substituent, $R_3$ is methyl, $R_2$ is ethylthio, $R_4$ is hydrogen, $X_1$ is =SO, G is —C(O)—O—CH=CH$_2$)

Following the procedure described in Example 1, 0.500 g (1.51 mmol) of 2-[(4-ethylthio-3-methyl-2-pyridinylmethyl(sulfinyl]-1H-benzimidazole and 0.192 g (1.81 mmol) of vinyl chloroformate furnished 0.280 g of the title compound as a tan colored crystalline solid, mp 120°–122° C. (dec).

Anal. Calc'd. for $C_{19}H_{19}N_3O_3S_2$: C, 56.86; H, 4.74; N, 10.47; S, 15.96. Found: C, 56.85; H, 4.76; N, 10.32; S, 15.77.

EXAMPLE 23

2-[(4-Ethylthio-3-methyl-2-pyridinylmethyl)sulfinyl]-1H-benzimidazole-1-carboisopropyloxy ester (Formula I: A and B are hydrogen, D is a Formula V substituent, $R_3$ is methyl, $R_2$ is ethylthio, $R_4$ is hydrogen, $X_1$ is =SO, G is —C(O)—O—CH(CH$_3$)$_2$)

Following the procedure described in Example 1, 0.500 g (1.51 mmol) of 2-[(4-ethylthio-3-methyl-2-pyridinylmethyl)sulfinyl]-1H-benzimidazole and 0.221 g (1.81 mmol) of isopropyl chloroformate gave 0.376 g of the title compound as a tan colored crystalline solid, mp 121°–123° C. (dec).

Anal. Calc'd. for $C_{20}H_{23}N_3O_3S_2$: C, 57.55; H, 5.52; N, 10.07; S, 15.35. Found: C, 57.48; H, 5.70; N, 9.91; S, 14.78.

EXAMPLE 24

2-[(4-Ethylthio-3-methyl-2-pyridinylmethyl)sulfinyl]-1H-benzimidazole-1-carbooctyloxy ester (Formula I: A and B are hydrogen, D is a Formula V substituent, $R_3$ is methyl, and $R_2$ is ethylthio, $R_4$ is hydrogen, $X_1$ is =SO, G is —C(O)—(CH$_2$)$_7$CH$_3$)

Following the procedure described in Example 1, 0.500 g (1.51 mmol) of 2-[(4-ethylthio-3-methyl-2-pyridinylmethyl)sulfinyl]-1H-benzimidazole and 0.350 g (1.81 mmol) of octyl chloroformate afforded 0.347 g of the title compound as a white crystalline solide, mp 61°–63° C.

Anal. Calc'd. for $C_{25}H_{33}N_3O_3S_2$: C, 61.60; H, 6.78; N, 8.62; S, 13.14. Found: C, 61.53; H, 6.68; N, 8.55; S, 13.08.

EXAMPLE 25

2[(4-Ethylthio-3-methyl-2-pyridinylmethyl)sulfinyl]-1θ-benzimidazole-1-carbo-(2-chloroethyloxy) ester (Formula I: A and B are hydrogen, D is a Formula V substituent, $R_3$ is methyl, and $R_2$ is ethylthio, $R_4$ is hydrogen, $X_1$ is =SO, G is C(O)—O—R$_6$, and R$_6$ is 2-chloroethyl)

Following the procedure described in Example 1, 0.500 g (1.51 mmol) of 2-[(4-ethylthio-3-methyl-2-pyridinylmethyl)sulfinyl]-1H-benzimidazole and 0.259 g (1.81 mmol) of 2-chloroethyl chloroformate gave 0.382 g of the title compound as a white crystalline solid, mp 122°–124° C. (dec).

Anal. Calc'd. for $C_{19}H_{20}ClN_3O_3S_2$: C, 52.17; H, 4.58; N, 9.61; S, 14.65. Found: C, 52.51; H, 5.02; N, 9.24; S, 13.74.

EXAMPLE 26

2-[(Ethylthio-3-methyl-2-pyridinylmethyl)sulfinyl]-1H-benzimidazole-1-carbo-(2,2,2-trichloro-1,1-dimethylethyloxy) ester (Formula I: A and B are hydrogen, D is a Formula V substituent, $R_3$ is methyl, $R_2$ is ethylthio, and $R_4$ is hydrogen, $X_1$ is =SO, G is —C(O)—O—R$_6$ and R$_6$ is 2,2,2-trichloro-1,1-dimethylethyl)

Following the procedure described in Example 17, 0.500 g (1.51 mmol) of 2-[(4-ethylthio-3-methyl-2-pyridinylmethyl)sulfinyl]-1H-benzimidazole and 0.471 g of (1.81 mmol) of 2,2,2-trichloro-1,1-dimethylethyl chloroformate provided 0.246 g of the title compound as a white crystalline solid, mp 162° C. (dec).

Anal. Calc'd. for $C_{21}H_{22}Cl_3N_3O_3S_2$: C, 47.10; H, 4.11; N, 7.85; S, 11.96. Found: C, 47.04; H, 4.31; N, 7.70; S, 11.70.

EXAMPLE 27

2-[(4-Ethylthio-3-methyl-2-pyridinylmethyl)sulfinyl]-1H-benzimidazole-1-(ethan-1-ol)ethyl ether To a magnetically stirred suspension of 60% sodium hydride (0.133 g, 3.32 mmol) in 25 ml of dimethylformamide was added under nitrogen 1.00 g (3.02 mmol) of 2-[(4-ethylthio-3-methyl-2-pyridinylmethyl)sulfinyl]-1H-benzimidazole as a solid. Stirring was continued at 25° C. for 15 min. To this reaction mixture was then added 0.392 g (3.62 mmol) of 1-chloroethyl ethyl ether and the contents stirred at 25° C. for an additional 30 min. The reaction mixture was then diluted with ethyl ether-ethylacetate solvent mixture and successively washed with saturated sodium bicarbonate, water, saturated brine and the organic solvent dried over anhydrous sodium sulfate. Concentration of the solvent in vacuo gave 130 g of the crude product. Chromatography of the crude product (silica gel, Skellysolve B-acetone, 3:1) afforded 0.913 g of the title compound as a mixture of two diastereomers. Recrystallization of this mixture from ethyl ether-Skellysolve B solvent mixtures gave 0.500 g of a 1:1 mixture of diastereomers (mp 107°–111° C.). Concentration of the mother liquor and recrystallization gave 0.237 g of a 9:1 mixture enriched with the more soluble diastereomer (mp 115°-117° C.).

EXAMPLE 28

2-[(3,5-Dimethyl-4-methoxy-2-pyridinylmethyl)sulfinyl]-1H-benzimidazole-1-(ethan-1-ol)acetyl ester To a magnetically stirred solution of 2-[(3,5-dimethyl-4-methoxy-2-pyridinylmethyl)thio]-1H-benzimidazole (0.670 g, 2.24 mmol) in 35 ml of acetonitrile was added 0.486 g (2.91 mmol) of α-bromoethylacetate. Stirring was continued at room temperature for 24 h. At the end of this period, the reaction mixture was diluted with ethyl acetate-ethyl ether (1:1) and the organic solvent washed with ice water, saturated brine and then dried over anhydrous sodium sulfate. Concentration of the solvent in vacuo yielded the crude product which was chromatographed on silica gel using methylene chloride-acetone (6:1) as the eluent to afford 0.201 g of 2-[(3,5-dimethyl-4-methoxy-2-pyridinylmethyl)thio]-1H-benzimidazole-1-(ethan-2-ol)acetyl ester.

The thioether obtained above (0.201 g, 0.52 mmol) was then dissolved in 20 ml of chloroform and the solution cooled in a 0°-5° C. ice-water bath. This cold solution was then treated with 0.55 mmol of m-chloroperoxybenzoic acid dissolved in 7 ml of chloroform. Stirring was continued at 0°-5° C. for 15 min. At the end of this time, the reaction mixture was diluted with additional chloroform, the chloroform solution washed with saturated sodium bicarbonate, saturated brine and dried over anhydrous sodium sulfate. Concentration of the solvent in vacuo gave the crude product which was chromatographed with silica gel using methylene choride-acetone (6:1) as the eluent to yield 91 mg of the title compound (mp 123°-124° C., recrystallized from Skellysolve B-ethyl ether solvent mixture.

EXAMPLE 29

General Procedure for the Oxidation of Thioether Derivatives

To a magnetically stirred solution of thioether in chloroform (0.1-0.2M), cooled in a 0°-5° C. ice-water bath, is added 1.0-1.1 equivalents of meta-chloriperbenzoic acid. Stirring is continued at 0°-5° C. for 15-20 min. The reaction is diluted with chloroform and the chloroform solution is then successively washed with saturated sodium bicarbonate solution, 10% sodium sulfite, saturated sodium bicarbonate solution, saturated brine and dired through anhydrous sodium sulfate. The chloroform solvent is removed in vacuo and the crude product purified by silica gel chromatography. Elution with ethyl acetate or solvent mixtures, such as ethyl acetate-methanol, acetone-Skellysolve B, yields the pure product.

Table I summarizes the compounds prepared by the above methods. Included in the table are some of their physical and chemical properties. In the Table, D is a substituent of the Formula V (i.e., a pyridinyl group), and A and B are hydrogen. All other variables are as defined in the table.

| Compound Name | G | X | $R_3$ | $R_2$ | $R_4$ | Melting Point $^1$H NMR (δ) | Anal. Calcd.: C, H, N, S Found: | High Resol. MS Calcd.: Found: |
|---|---|---|---|---|---|---|---|---|
| 2-((2-Pyridinylmethyl)-sulfinyl)-1H—benzimidazole-1-methanol, acetate (ester) | $CH_3C(O)$— $m = 1, R_{10} = H$ | =SO | H | H | H | 99-100° C. 8.70, 6.45, 4.95, 2.07 | $C_{16}H_{15}N_3O_3S$: 58.36, 4.56, 12.77, 9.73 58.22, 4.50, 12.75, 9.79 | $C_{16}H_{15}N_3O_3SK$: 368.0471 368.0451 |
| 2-((2-Pyridinylmethyl)-sulfinyl)-1H—benzimidazole-1-methanol, octanoate (ester) | $CH_3(CH_2)_5$—$C(O)$— $m = 1, R_{10} = H$ | =SO | H | H | H | 48-50° C. 8.60, 6.45, 4.97, 2.30, 0.88 | $C_{22}H_{27}N_3O_3S$: 63.89, 6.58, 10.16, 7.75 63.70, 6.61 10.11, 7.63 | $C_{22}H_{27}N_3O_3SK$: 452.1410 452.1428 |
| 2-((2-Pyridinylmethyl)-sulfinyl)-1H-13 benzimidazole-1-methanol-2-methyl-propanoate (ester) | $(CH_3)_2$—CH—$C(O)$— $m = 1, R_{10} = H$ | =SO | H | H | H | 69-71° C. 8.60, 6.47, 4.98, 2.55, 1.10 | $C_{18}H_{19}N_3O_3S$: 60.49, 5.36, 11.76, 8.97 59.91, 5.33, 11.61, 8.65 | $C_{18}H_{19}N_3O_3SK$: 396.0784 396.0805 |
| 2-((2-Pyridinylmethyl)-sulfinyl)-1H—benzimidazole-1-methanol-4-methoxy-4-oxobutanoate (ester) | $CH_3CO_2$—$(CH_2)_2$—$C(O)$— $m = 1, R_{10} = H$ | =SO | H | H | H | 114-115° C. 8.62, 6.48, 4.99, 3.60, 2.65 | $C_{19}H_{19}N_3O_5S$: 56.85, 4.77, 10.47, 7.99 56.52, 4.94, 10.35, 8.03 | $C_{19}H_{20}N_3O_5S$: (M+H) 402.1124 402.1130 |
| 2-((2-Pyridinylmethyl)-sulfinyl)-1H—benzimidazole-1-methanol-(2-methyl-propyl carbonate) (ester) | $(CH_2)_2C$—$O$—$C(O)$— $m = 1, R_{10} = H$ | =SO | H | H | H | 78-81° C. 8.62, 6.49, 4.95, 3.95 1.90, 0.88 10.74, 8.24 | $C_{19}H_{21}N_3O_4S$: 58.90, 5.46, 10.84, 8.28 58.52, 5.47, | $C_{19}H_{21}N_3O_4SK$: 426.0890 426.0884 |

FORMULAS

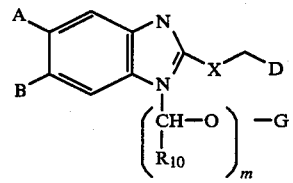

I

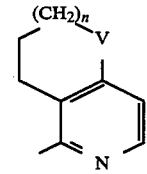

II

-continued
FORMULAS

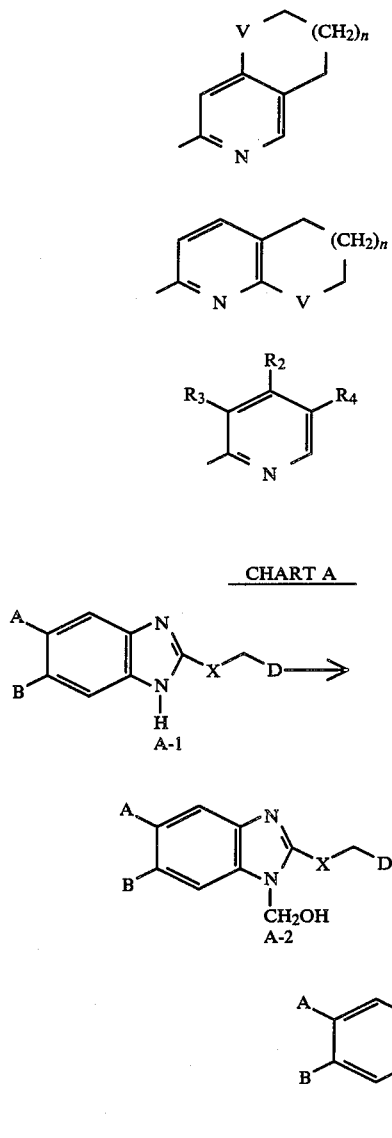

CHART A

A-1

A-2

A-3

CHART B

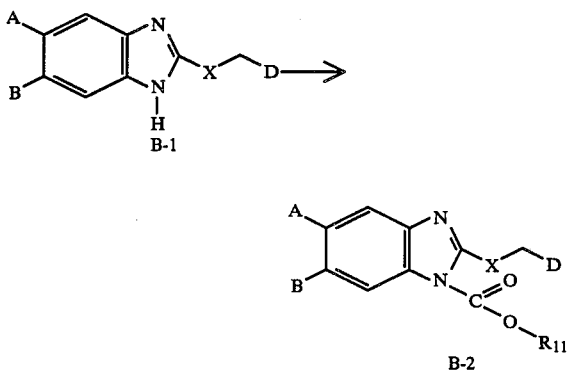

B-1

B-2

CHART C

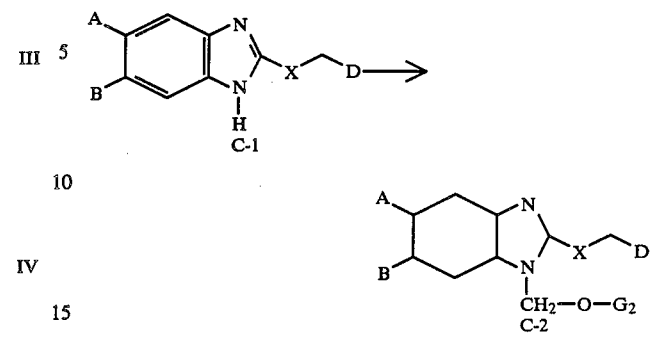

C-1

C-2

CHART D

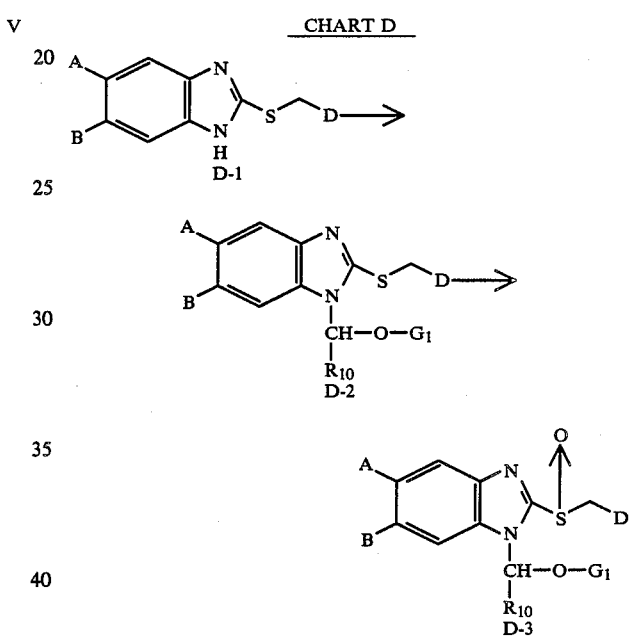

D-1

D-2

D-3

We claim:

1. A compound selected from the group consisting of:
2-[(2-pyridinylmethyl)sulfinyl]-1H-benzimidazole-1-methanol,
2[(4-methoxy-3,5-dimethyl-2-pyridinylmethyl)-thio]-1H-benzimidazole-1-methanol,
2-[(4-ethylthio-3-methyl-2-pyridinylmethyl)thio]-1H-benzimidazole-1-methanol,
2-[(4-chloro-3-methyl-2-pyridinylmethyl)thio]-1H-benzimidazole-1-methanol,
2-[(4-methoxy-3,5-dimethyl)-2-pyridinylmethyl)thio-1H-benzimidazole-1-methanol, acetate (ester),
2-[(2-pyridinylmethyl)thio]-1H-benzimidazole-1-methanol, acetate (ester),
2-[(4-ethylthio-3-methyl-2-pyridinylmethyl)thio]-1H-benzimidazole-1-methanol, acetate (ester),
2-[(4-chloro-3-methyl-2-pyridinylmethyl)thio]-1H-benzimidazole-1-methanol, acetate (ester),
2-[(2-pyridinylmethyl)thio]-1H-benzimidazole-1-methanol, methyl succinate (ester),
2-[(2-pyridinylmethyl)thio]-1H-benzimidazole-1-methanol, octanoate (ester),
2-[(2-pyridinylmethyl)thio]-1H-benzimidazole-1-methanol, isobutyrate (ester), and 2-[(2-pyridinylmethyl)thio]-1H-benzimidazole-1-methanol, isopropionate (ester).

2. A compound selected from the group consisting of:
2-((2-pyridinylmethyl)sulfinyl)-1H-benzimidazole-1-methanol, acetate (ester),
2-((2-pyridinylmethyl)sulfinyl)-1H-benzimidazole-1-methanol, octanoate (ester),
2-((2-pyridinylmethyl)sulfinyl)-1H-benzimidazole-1-methanol-(2-methylpropanoate (ester),
2-((2-pyridinylmethyl)sulfinyl)-1H-benzimidazole-1-methanol-4-methoxy-4-oxobutanoate (ester),
2-((2-pyridinylmethyl)sulfinyl)-1H-benzimidazole-1-methanol-2-methyl propionate (ester),
2-(((4-methoxy-3,5-dimethyl-2-pyridinyl)methyl)sulfinyl)-1H-benzimidazole, 1-methanol acetate (ester),
2-(((4-ethylthio-3-methyl-2-pyridinyl)methyl)-sulfinyl)-1H-benzimidazole-1-methanol, acetate (ester), and
2-(((4-chloro-3-methyl-2-pyridinyl)methyl)-sulfinyl)-1H-benzimidazole-1-methanol, acetate (ester).

3. A compound selected from the group consisting of:
2-[(3,5-Dimethyl-4-methoxy-2-pyridinylmethyl)sulfinyl]-1H-benzimidazole-1-(ethan-1-ol)acetyl ester;
2-[(2-pyridinylmethyl)sulfinyl]-1H-benzimidazole-1-(ethan-1-ol)acetyl ester, more polar diastereomer;
2-[(2-pyridinylmethyl)sulfinyl]-1H-benzimidazole-1-(ethan-1-ol)acetyl ester, less polar diastereomer;
2-[(2-pyridinylmethyl)sulfinyl]-1H-benzimidazole-1-(ethan-1-ol)benzoyl ester, less polar diastereomer;
2-[(2-pyridinylmethyl)sulfinyl]-1H-benzimidazole-1-ethan-1-ol)benzoyl ester, more pure diastereomer;
2-[(2-pyridinylmethyl)sulfinyl]-1H-benzimidazole-1-(ethan-1-ol)tertbutyl carbonyl ester, more polar diastereomer;
2-[(2-pyridinylmethyl)sulfinyl]-1H-benzimidazole-1-(ethan-1-ol)tertbutyl carbonyl ester, less polar diastereomer;
2-[(3,5-dimethyl-4-methoxy-2-pyridinylmethyl)sulfinyl]-1H-benzimidazole-1-(ethan-1-ol)ethyl ether;
2-[(2-ethylthio-3-methyl-2-pyridinylmethyl)sulfinyl]-1H-benzimidazole-1-methanol methyl ester;
2-[(2-pyridinylmethyl)sulfinyl]-1H-benzimidazole-1-(ethan-1-ol)-ethyl ether;
2-[(4-ethylthio-3-methyl-2-pyridinylmethyl)sulfinyl]-1H-benzimidazole-1-(ethan-1-ol)ethyl ether; and
2-[(4-ethylthio-3-methyl-2-pyridinylmethyl)thio]-1H-benzimidazole-1-(ethan-1-ol)ethyl ether.

* * * * *